(12) United States Patent
Kolosova

(10) Patent No.: US 8,715,753 B1
(45) Date of Patent: May 6, 2014

(54) FORMULATION FOR ELIMINATING BEDBUGS

(76) Inventor: Nadia Kolosova, Linwood, PA (US)

( * ) Notice: Subject to any disclaimer, the term of this patent is extended or adjusted under 35 U.S.C. 154(b) by 78 days.

(21) Appl. No.: 13/272,605

(22) Filed: Oct. 13, 2011

(51) Int. Cl.
*A61K 36/31* (2006.01)
*A61K 36/00* (2006.01)
*A61K 36/899* (2006.01)

(52) U.S. Cl.
CPC .............. *A61K 36/31* (2013.01); *A61K 36/899* (2013.01)
USPC .......................................... 424/755; 424/776

(58) Field of Classification Search
None
See application file for complete search history.

(56) References Cited

U.S. PATENT DOCUMENTS

| 3,090,720 A | 5/1963 | Kenaga |
| 5,206,022 A | 4/1993 | Nichols |
| 7,232,844 B2 | 6/2007 | Hallahan |
| 7,381,431 B2 | 6/2008 | Baker et al. |
| 2004/0166135 A1* | 8/2004 | Koos et al. ................ 424/405 |
| 2006/0251747 A1* | 11/2006 | Ritchie ..................... 424/755 |
| 2006/0269582 A1 | 11/2006 | Bruins et al. |

FOREIGN PATENT DOCUMENTS

| FR | 2773674 A1 * | 7/1999 |
| JP | 76030147 B * | 8/1976 |

OTHER PUBLICATIONS

Website document entitled "Colman's of Norwich: English Mustard" (available at http://colmans.co.uk/our-range/mustards/english-mustard). Dowloaded from website: Mar. 12, 2013.*

* cited by examiner

*Primary Examiner* — Chris R Tate
*Assistant Examiner* — Russell Fiebig

(57) ABSTRACT

A formulation for eliminating bedbugs containing mustard powder and water and optionally flour or a starch such as cornstarch. The ratio of mustard powder to water may be about 2 grams mustard powder to about 10 mL water. The ratio of flour to water is about 3 grams flour to about 10 mL water.

2 Claims, No Drawings

FORMULATION FOR ELIMINATING BEDBUGS

FIELD OF THE INVENTION

The present invention is directed to a formula for eliminating bedbugs.

BACKGROUND OF THE INVENTION

Bedbugs are an extremely common problem. They infest homes, apartments, hotels and motels, and other areas. The present invention features a novel mixture for eliminating bedbugs.

Any feature or combination of features described herein are included within the scope of the present invention provided that the features included in any such combination are not mutually inconsistent as will be apparent from the context, this specification, and the knowledge of one of ordinary skis in the art. Additional advantages and aspects of the present invention are apparent in the following detailed description and claims.

SUMMARY

The present invention features a formulation for eliminating bedbugs. The formulation comprises mustard powder and water. In some embodiments, the ratio of mustard powder to water is about 2 grams mustard powder to about 10 mL water. In some embodiments, the ratio of mustard powder to water is about 1 gram mustard powder to about 15 mL water.

In some embodiments, the formulation further comprises flour. In some embodiments, the ratio of flour to water is about 3 grams flour to about 10 mL water. In some embodiments, the ratio of flour to water is about 4 grams flour to about 10 mL water. In some embodiments, the formulation further comprises starch. In some embodiments, the starch is corn starch. In some embodiments, the ratio of starch to water is about 5 grams starch to about 10 mL water. In some embodiments, the ratio of starch to water is about 10 grams starch to about 10 mL water.

DESCRIPTION OF PREFERRED EMBODIMENTS

The present invention features a novel formulation for eliminating bedbugs. The formulation comprises mustard powder and water. In some embodiments, the formulation further comprises flour or a starch (e.g., corn starch). The ratio of the flour or starch to water depends on where the formulation is applied, for example to the wall, the floor, or other locations. For example, the formulation may be made thinner so that is sprayable onto a wall surface.

In some embodiments, the ratio of mustard powder to water is about 1 gram to about 10 mL. In some embodiments, the ratio of mustard powder to water is about 1 gram to 5 mL. In some embodiments, the ratio of mustard powder to water is about 1 gram to 2.5 mL. In some embodiments, the ratio of mustard powder to water is about 1 gram to 6 mL. In some embodiments, the ratio of mustard powder to water is about 1 gram to 7 mL. In some embodiments, the ratio of mustard powder to water is about 1 gram to 8 mL. In some embodiments, the ratio of mustard powder to water is about 1 gram to 9 mL. In some embodiments, the ratio of mustard powder to water is about 1 gram to 15 mL. In some embodiments, the ratio of mustard powder to water is about 1 gram to 20 mL.

In some embodiments, the formulation further comprises flour. For example, in some embodiments, the ratio of flour to water is about 1 gram of flour to about 10 mL of water. In some embodiments, the ratio of flour to water is about 2 grams of flour to about 10 mL of water. In some embodiments, the ratio of flour to water is about 3 grams of flour to about 10 mL of water. In some embodiments, the ratio of flour to water is about 4 grams of flour to about 10 mL of water. In some embodiments, the ratio of flour to water is about 1 gram of flour to about 20 mL of water. In some embodiments, the ratio of flour to water is about 1 gram of flour to about 30 mL of water.

In some embodiments, the formulation further comprises starch (e.g., corn starch). For example, in some embodiments, the ratio of starch to water is about 1 gram of starch to about 10 mL of water. In some embodiments, the ratio of starch to water is about 2 grams of starch to about 10 mL of water. In some embodiments, the ratio of starch to water is about 3 grams of starch to about 10 mL of water. In some embodiments, the ratio of starch to water is about 4 grams of starch to about 10 mL of water. In some embodiments, the ratio of starch to water is about 1 gram of starch to about 20 mL of water. In some embodiments, the ratio of starch to water is about 1 gram of starch to about 30 mL of water.

To make the formulation with the starch, the water is first boiled and the starch is added subsequently. If the formulation is made with flour, the water does not need to be boiled first.

As used herein, the term "about" refers to plus or minus 10% of the referenced number. For example, an embodiment wherein the formulation comprises about 1 gram of mustard powder includes a formulation that comprises between 0.9 and 1.1 grams of mustard powder.

The disclosures of the following U.S. Patents are incorporated in their entirety by reference herein: U.S. Pat. No. 3,090,720; U.S. Pat. No. 5,206,022; U.S. Pat. No. 7,232,844; U.S. Pat. No. 7,381,431; U.S. Patent Application No. 2004/0166135; U.S. Patent Application No. 2006/0269582.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A method of eliminating beg bugs (*Cimex lectularius*) from an infected area, the method consisting of:
   (a) formulating a composition consisting of mustard powder and water in a ratio of 1:40;
   (b) applying said composition in an infected area where bed bugs are found, and thereby eliminating the bed bugs.

2. A method of eliminating beg bugs (*Cimex lectularius*) from an infected area, the method consisting of:
   (a) formulating a composition consisting of mustard powder, cornstarch and water;
   (b) applying said composition in an infected area where bed bugs are found, and thereby eliminating the bed bugs; wherein the ratio of mustard powder to water is 1:40, and wherein the cornstarch is added to the composition in an effective amount depending upon the desired consistency of the composition.

\* \* \* \* \*